(12) United States Patent
Rubel

(10) Patent No.: US 12,685,303 B2
(45) Date of Patent: *Jul. 21, 2026

(54) LIGHTING ELEMENT WITH INSECT REPELLING ELEMENT

(71) Applicant: PIC Corporation, Linden, NJ (US)

(72) Inventor: Eric Rubel, Westfield, NJ (US)

(73) Assignee: PIC Corporation, Clark, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/974,023

(22) Filed: Dec. 9, 2024

(65) Prior Publication Data

US 2025/0098662 A1     Mar. 27, 2025

Related U.S. Application Data

(63) Continuation of application No. 17/749,519, filed on May 20, 2022, now Pat. No. 12,193,432, which is a continuation of application No. 16/570,565, filed on Sep. 13, 2019, now Pat. No. 11,363,810.

(60) Provisional application No. 62/730,794, filed on Sep. 13, 2018.

(51) Int. Cl.
| | |
|---|---|
| *A01M 29/00* | (2011.01) |
| *A01M 29/12* | (2011.01) |
| *F21K 9/237* | (2016.01) |
| *A01M 1/20* | (2006.01) |
| *A61L 9/03* | (2006.01) |
| *F21Y 115/10* | (2016.01) |

(52) U.S. Cl.
CPC ............ *A01M 29/00* (2013.01); *A01M 29/12* (2013.01); *F21K 9/237* (2016.08); *A01M 1/2077* (2013.01); *A61L 9/037* (2013.01); *A61L 2209/12* (2013.01); *A61L 2209/133* (2013.01); *F21Y 2115/10* (2016.08)

(58) Field of Classification Search
CPC .......... A61L 2209/12; A61L 2209/133; A01M 29/12; A01M 1/2077; A01M 1/2083; F21K 9/237; B05B 7/1686
See application file for complete search history.

(56) References Cited

U.S. PATENT DOCUMENTS

| | | | |
|---|---|---|---|
| 4,371,087 | A | 2/1983 | Saujet |
| 4,822,613 | A * | 4/1989 | Rodero ................. A01N 25/16 |
| | | | 424/405 |
| 7,503,675 | B2 | 3/2009 | Demarest et al. |
| 7,618,151 | B2 * | 11/2009 | Abbondanzio ........... A61L 9/03 |
| | | | 362/253 |
| 7,641,364 | B2 * | 1/2010 | Abbondanzio ........ H05B 45/20 |
| | | | 362/253 |
| 8,027,575 | B2 * | 9/2011 | Hasik ........................ A61L 9/03 |
| | | | 392/394 |
| 9,968,080 | B1 * | 5/2018 | Van Kleef ............. A01M 29/10 |

(Continued)

OTHER PUBLICATIONS

International Search Report and Written Opinion dated Dec. 5, 2019 issued in corresponding PCT International Application No. PCT/US2019/051105.

(Continued)

*Primary Examiner* — Tracie Y Green
*Assistant Examiner* — Michael Chiang
(74) *Attorney, Agent, or Firm* — Amster, Rothstein & Ebenstein LLP

(57) ABSTRACT

The present invention relates to a lighting element including an insect repelling element.

19 Claims, 11 Drawing Sheets

(56) References Cited

U.S. PATENT DOCUMENTS

| | | | | |
|---|---|---|---|---|
| 11,363,810 | B2 * | 6/2022 | Rubel | F21K 9/237 |
| 11,771,073 | B2 | 10/2023 | Smith et al. | |
| 12,193,432 | B2 * | 1/2025 | Rubel | F21K 9/237 |
| 2004/0180070 | A1 | 9/2004 | Inoue et al. | |
| 2005/0133617 | A1 * | 6/2005 | Hidalgo | A61L 9/02 239/44 |
| 2006/0237439 | A1 * | 10/2006 | Norwood | A61L 9/03 219/506 |
| 2007/0014549 | A1 * | 1/2007 | Demarest | H05B 35/00 392/393 |
| 2007/0086199 | A1 * | 4/2007 | Demarest | H01R 33/94 362/441 |
| 2007/0109763 | A1 * | 5/2007 | Wolf | A01M 1/2083 362/276 |
| 2008/0036332 | A1 * | 2/2008 | Helf | A61L 9/14 310/311 |
| 2009/0200393 | A1 * | 8/2009 | Avelar | C11C 5/006 239/60 |
| 2015/0144712 | A1 * | 5/2015 | Formico | A01M 1/2044 239/289 |
| 2017/0303523 | A1 | 10/2017 | Sandford et al. | |
| 2017/0367314 | A1 | 12/2017 | Billingsley, Jr. | |
| 2018/0199563 | A1 | 7/2018 | Zheng et al. | |
| 2019/0281810 | A1 * | 9/2019 | Sinur | A01M 29/12 |

OTHER PUBLICATIONS

Chinese Office Action dated Jan. 6, 2022 issued in Chinese Patent Application No. 201980059909.5, with English language translation.

* cited by examiner

LIGHTING ELEMENT WITH INSECT REPELLING ELEMENT

CROSS-REFERENCE TO RELATED APPLICATIONS

The present application is a continuation of U.S. patent application Ser. No. 17/749,519, filed May 20, 2022, which is a continuation of U.S. patent application Ser. No. 16/570, 565, filed Sep. 13, 2019, now U.S. Pat. No. 11,363,810, which claims benefit of and priority to U.S. Provisional Patent Application No. 62/730,794 entitled LIGHTING ELEMENT WITH FRAGRANCE BASED INSECT REPELLING ELEMENT filed Sep. 13, 2018, the entire content of which is hereby incorporated by reference herein.

BACKGROUND

Field of the Disclosure

The present invention generally relates to pest management. More specifically, the present invention relates to a lighting element that includes an insect repelling element.

Related Art

During mild weather, many people enjoy spending additional time outside, during both daytime and nighttime hours. One drawback of spending time outdoors during mild weather, however, is that insect activity often increases at this time. In addition, as people turn on lights when the sun goes down, the light tends to attract more insects such that it is often difficult to enjoy the outdoors.

Accordingly, it would be useful to provide a lighting element that avoids the above and other problems.

SUMMARY

An object of the present invention is to provide a lighting element that includes an insect repelling element.

A lighting element in accordance with an embodiment of the present disclosure includes: an electrical connector; a body extending from the electrical connector, the body including a plurality of openings formed in a side thereof; a heating element mounted in the body and electrically connected to the electrical connector; an insect repelling material cartridge including insect repelling material, the insect repelling material cartridge removably mounted in the body, the insect repelling material cartridge including: a bottom; sidewalls extending upward from the bottom to form a cavity, where the cavity receives the insect repelling material; an open top; and a wick extending from the cavity to the open top to transfer insect repelling material from the cavity of the container, where the insect repelling material cartridge is mounted in the housing such that a top portion of the wick is adjacent to the heating element such that heat from the heating element vaporizes the insect repelling material in the wick; and a light source, mounted on a bottom of the housing and electrically connected to the electrical connector, the light source configured to emit light.

In embodiments, the lighting element may include a plurality of vertical ribs extending away from the electrical connector where the plurality of openings are spaced between the plurality of vertical ribs.

In embodiments, each opening of the plurality of openings is sized such that a user's finger will not fit into the respective opening.

In embodiments, the heating element is disk shaped.

In embodiments, the heating element includes a central opening formed therethrough, and the insect repelling material cartridge is mounted in the body such that at least a portion of the wick extends into the central opening of the heating element.

In embodiments, the heating element includes positive temperature coefficient material configured to produce heat; and a conducting ring positioned around an inner surface of the central opening to conduct heat toward the wick.

In embodiments, the insect repelling material cartridge further comprises an insert configured to be mounted in the open top of the insect repelling material cartridge, the insert including a wick opening formed therein to allow the wick to pass through the insert while preventing insect repelling material from passing around the inlet and out of the insect repelling material cartridge.

In embodiments, the insect repelling material is provided in an immersive foam solvent.

In embodiments, the insect repelling material is at least one of the group comprising a liquid, a polymer and a gel.

In embodiments, the insect repelling material comprises metofluthrin.

In embodiments, the housing further comprises a receptacle formed in a bottom portion thereof.

In embodiments, the insect repelling material cartridge is removably mounted in the receptacle.

In embodiments, the insect repelling material cartridge further comprises a tab extending from a bottom surface of the bottom and configured to allow a user to rotate the insect repelling material cartridge in the receptacle to secure the insect repelling material cartridge in the receptacle when rotated in a first direction and to remove the insect repelling material cartridge from the receptacle when rotated in a second direction, opposite the first direction.

In embodiments, the housing includes: a lower protrusion extending upward from an inner surface of a bottom portion of the housing and positioned below the heating element; and an upper protrusion extending downward from an inner surface of a top portion of the housing above the heating element, wherein the upper protrusion and lower protrusion are configured such that air flows along the surface of one of the upper protrusion and the lower protrusion toward the heating element and then along the surface of the other of the upper protrusion and the lower protrusion and then out through the plurality of openings.

In embodiments, the lighting element includes at least one indicator configured to indicate that the heating element is active.

In embodiments, the at least one indicator is a light emitting diode.

In embodiments, the at least one indicator is a transducer that emits sound.

In embodiments, the light source is a light emitting diode.

In embodiments, the light source includes a cover element positioned to cover the light emitting diode.

In embodiments, the cover element may be colored.

This and other objects shall be addressed by embodiments of the present invention as set forth herein.

BRIEF DESCRIPTION OF THE DRAWINGS

Exemplary embodiments of the present invention will be described with references to the accompanying figures, wherein.

DETAILED DESCRIPTION

The present invention generally relates to a lighting element including an insect repelling element and more specifically to a lighting element that includes a fragrance based insect repelling element.

Figure 1:
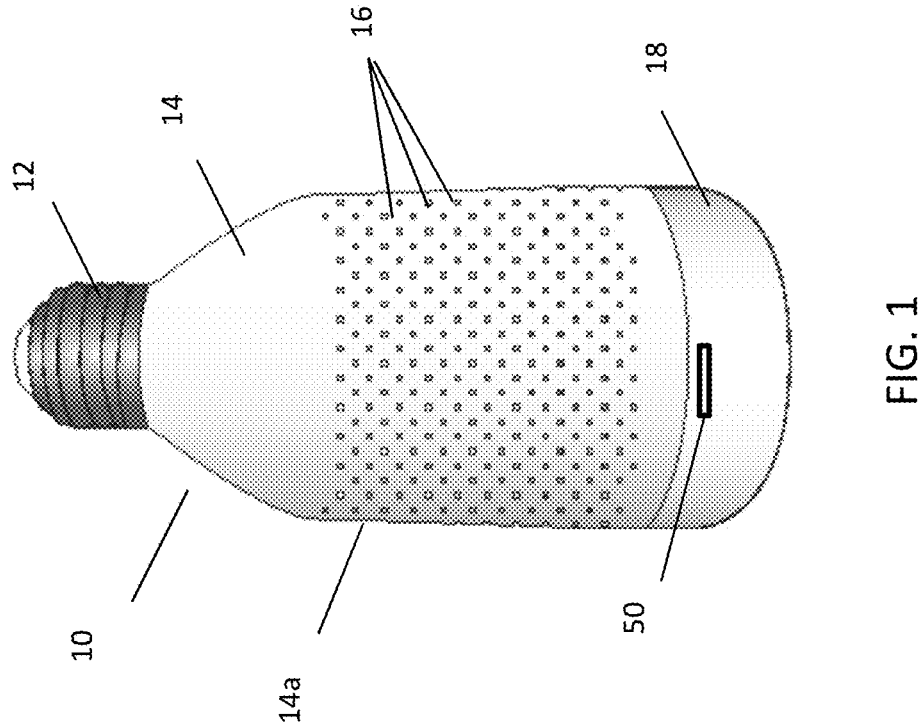
FIG. 1 illustrates a lighting element including an insect repelling element in accordance with an embodiment of the present disclosure.

FIG. 1 illustrates an exemplary embodiment of a lighting element 10 in accordance with an embodiment of the present disclosure. In embodiments, the lighting element 10 may include an Edison-type connector 12 suitable for connection to conventional light sockets to provide electricity. In embodiments, the connector 12 may be an E26 screw lamp holder. While an Edison-type connector 12 is illustrated in FIG. 1, any suitable connector may be used. In embodiments, the lighting element 10 may include a body 14 extending away from the connector 12 and including a plurality of openings 16 formed therein. In embodiments, the openings 16 are provided substantially around the entire periphery of the body 14, however, different patterns and positioning of the openings 16 may be used, as desired. In embodiments, the openings 16 may be formed in a sidewall 14a of the body 14.

Figure 2:
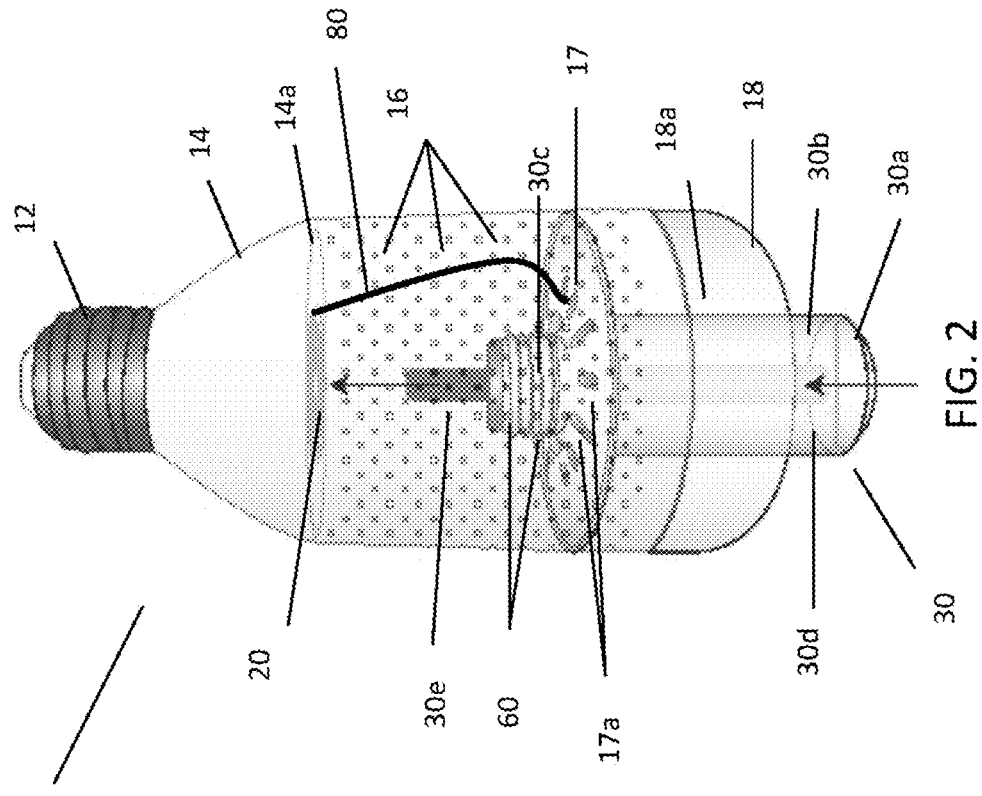
FIG. 2 illustrates the lighting element of FIG. 1 with a transparent sidewall such that an interior thereof is visible in accordance with an embodiment of the present disclosure.

FIG. 2 illustrates the lighting element 10 with the sidewall 14a of the body 14 presented as transparent such that the interior of the housing is visible. In embodiments, the body 14 may be transparent or opaque, as desired. In embodiments, a heating element 20 may be provided within the sidewall 14a of the housing 14. In embodiments, the heating element 20 may be positioned in a top portion of the housing 14. In embodiments, the heating element 20 may be positioned in any desired position in the housing 14. In embodiments, the heating element 20 may be disk shaped, however, other shapes may be used. In embodiments, the heating element 20 may be powered electrically via power provided from the connector 12. In embodiments, the heating element 20 may be directly connected to the connector 12. In embodiments, a heating circuit (not shown) may be provided between the connector 12 and the heating element 20 to provide power to the heating element. In embodiments, the heating circuit may be provided on a printed circuit board. In embodiments, the heating circuit may be implemented using discrete circuit elements. In embodiments, the heating circuit may be embodied as a processor or connected to and/or controlled by a processor or other control circuit.

As illustrated in FIG. 2, in embodiments, an insect repelling material cartridge, or fragrance cartridge 30 may be mounted inside the housing 14. The insect repelling material cartridge 30 may include a bottom element 30a with a sidewall 30b extending upward therefrom to a top member 30c. In embodiments, the insect repelling material cartridge 30 may include an internal cavity 30d formed by the bottom element 30a and the sidewall 30b that may contain an insect repelling material. In embodiments, the insect repelling material may include fragrant material to provide a pleasant odor. The insect repelling material may be in the form of a liquid, polymer and/or a gel, to name a few. The cartridge 30 may also include a wick element 30e that extends into the cavity 30d and into the insect repelling material and out of a top portion 30c of the cartridge 30. The insect repelling material may be transported through the wick 30e to the top portion thereof, above the top portion 30c of the cartridge 30, and preferably adjacent to the heating element 20 such that heat from the heating element vaporizes the insect repelling material. In embodiments, the insect repelling material may be an insect repellant, which, after it is vaporized by the heating element 20, passes through the openings 16 and outward around the lighting element 10. As a result, a zone of vaporized insect repellant will surround the lighting element 10 which will deter insects from entering this zone. In embodiments, the insect repelling material may include insect repellant as well as an air freshening material such that the vaporized material will deter insects and will also provide a pleasant smell. In embodiments the insect repellant may include metofluthrin, however, other insect repellants may be used. In embodiments, the insect repelling material may be an air freshener only.

In embodiments, the cartridge 30 may be removably mounted in the housing 14. In embodiments, the housing 14 may include fitting 17 which receives the cartridge 30. In embodiments, the cartridge 30 may include threads 60 which may interact with the fitting 17 to secure the cartridge in the housing 14. In embodiments, the fitting 17 may be annular in shape and include a central opening with complimentary threads 70. In embodiments, the fitting 17 may include one or more slots 17a such that vaporized insect repelling material and/or fragrant material may pass through the slots as well as the openings 16 in the housing 14. In embodiments, the fitting 17 and the cartridge 30 may be structured and positioned such that the wick 30e is positioned adjacent to the heating element 20 when the cartridge is mounted in the housing 14. In embodiments, the bottom of the cartridge 30a may include a tab 30f extending therefrom that may be gripped by a user to rotate the cartridge 30 in a first direction to secure the cartridge to the housing 14 and/or in a second direction to remove the cartridge from the housing.

In embodiments, a light source 18 may be provided on a bottom portion of the housing 14. In embodiments, the light source 18 may be implemented in the form of one or more light emitting diodes (LEDs) 18b. In embodiments, the light source 18 may be implemented as any other suitable light source. In embodiments, the light source 18 may be electrically powered with power provided via the connector 12. In embodiments, the light source 18 may be directly connected to the connector 12. In embodiments, a light circuit (not shown) may be provided between the connector 12 and the light source 18 to provide power to the light source. In embodiments, one or more wires 80 may extend from the connector 12 to the light source 18 and/or heating element 20. In embodiments, the light circuit may be provided on a printed circuit board. In embodiments, the light circuit may be implemented as discrete circuit elements. In embodiments, the light circuit may be embodied as a processor or connected to and/or controlled by a processor or other control element or circuit. In embodiment, the light circuit may be provided with or adjacent to the heating circuit discussed above. In embodiments, both the heating circuit and light circuit may be provided on a printed circuit board. In embodiments, the heating circuit and light circuit may be provided on the same printed circuit board. In embodiments, the heating circuit and light circuit may be provided on different printed circuit boards. In embodiments, a lamp lens or other cover 18a may cover the LEDs or other light elements. In embodiments, the cover 18a may be substantially transparent. In embodiments, the cover 18a may be substantially opaque. In embodiments the cover 18a may be partially opaque. In embodiments, the cover 18a may be colored to provide for a colored light.

Figure 2A:
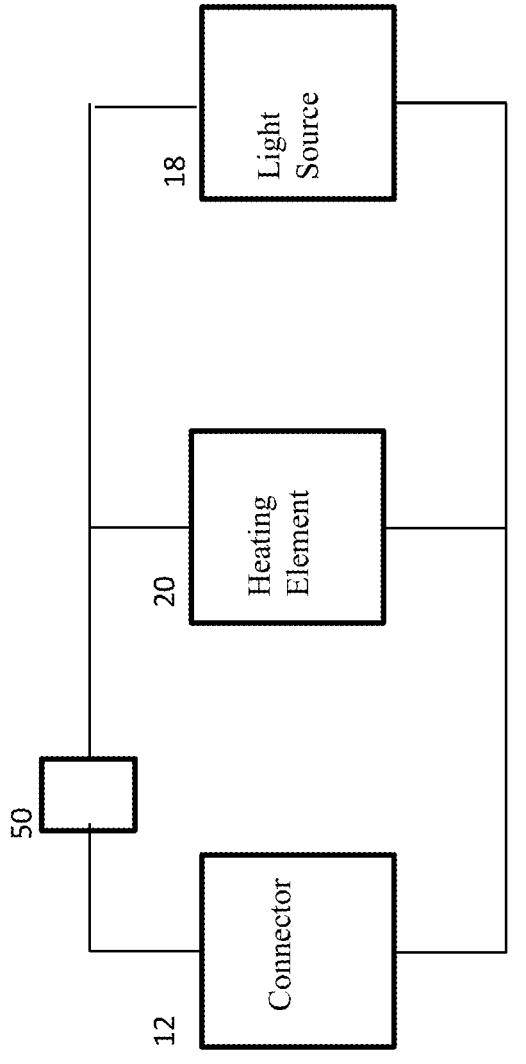
FIG. 2A is an exemplary block diagram illustrating a connection between an electrical connector, a switch, a heating element and a light source of the lighting element of FIG. 1.
Figure 3:
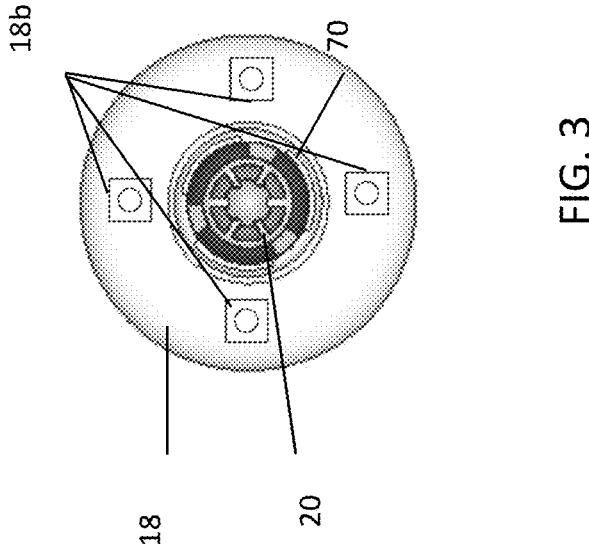
FIG. 3 illustrates a bottom view of the lighting element of FIGS. 1-2 in accordance with an embodiment of the present disclosure.
Figure 4:
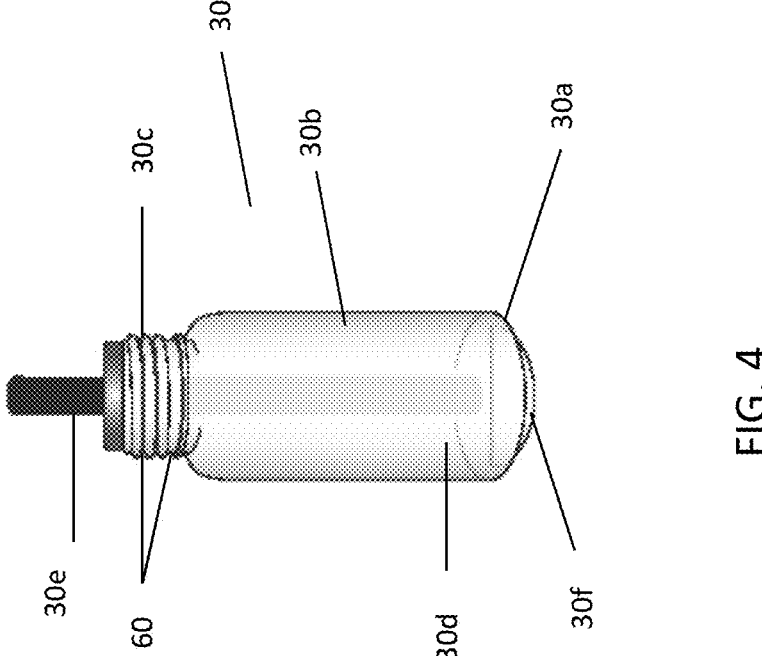
FIG. 4 is a more detailed view of an insect repelling material cartridge that is mountable in the lighting element of FIGS. 1-2.
Figure 5:
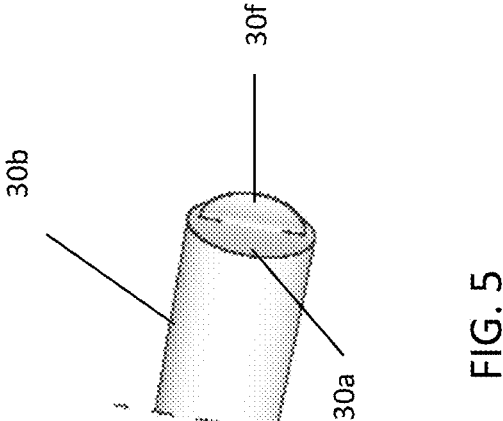
FIG. 5 is a more detailed view of the lower portion of the insect repelling material cartridge of FIG. 4 in accordance with an embodiment of the present disclosure.

In embodiments, both the heating element 20 and the light source 18 may be selectably activated by a user. In embodiments, one or more switches 50 may be provided to control power delivered to the heating element 20 and/or the light source 18. FIG. 2A illustrates an exemplary block diagram illustrating an exemplary connection between the connector 12 which provides power, via switch 50, to the heating element 20 and light source 18 (or a light element thereof). While a single switch 50 is illustrated in FIG. 2, additional switches may be provided to allow for control of the heating element 20 and the light source 18 independently. In embodiments, the switch 50 may be a multiple position switch to allow for control of the heating element 20 and the light source 18 independently or together. In embodiments, the switch 50 may be embodied as a programmable device or controller to allow for control of the heating element 20 and the light source 18 independently or together. In embodiments, one or more timers may be used to control activation of the heating element 20 and/or light source 18. In embodiments, one or more timers may be used in combination with the one or more switches. In embodiments, the timers may be used to activate the one or more switches. In embodiments, the one or more switches may be used to activate or deactivate the one or more timers. In embodiments, one or more light sensors may be provided and activation of the heating element 20 and/or light source 18 may be based on a detected light level. In embodiments, the heating element 20 may be activated without activating the light source 18 to provide for insect repelling even when the light is unnecessary, for example, during the day. In embodiments, the light element 18 may be activated while the heating element 20 remains inactive such that light can be provided even if there is no need for insect repellant. Both the light source 18 and heating element 20 may be activated at the same time to provide light as well as insect repellant. The light source 18 and heating element 20 may be deactivated at the same time as well.

Figure 6:
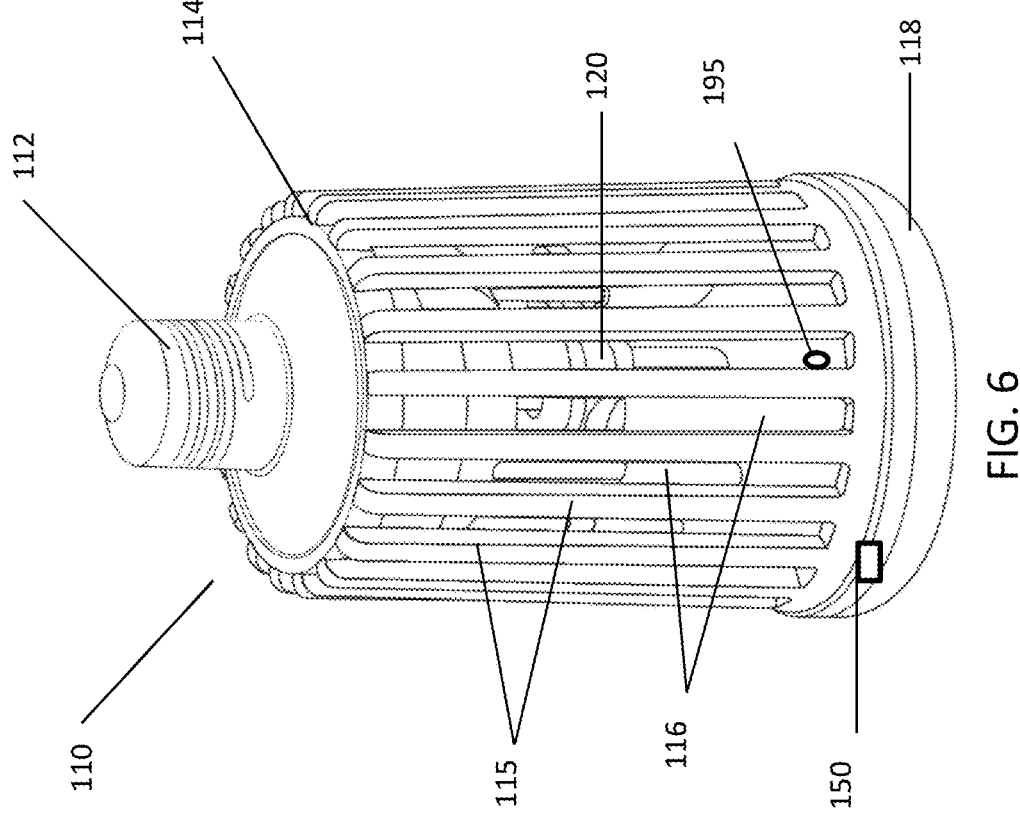
FIG. 6 illustrates a lighting element including an insect repelling element in accordance with an embodiment of the present disclosure.

FIG. 6 illustrates another embodiment of a lighting element 110 in accordance with an embodiment of the present disclosure. In embodiments, the lighting element 110 may include an Edison-type connector 112 suitable for connection to conventional light sockets. In embodiments, the connector 112 may be an E26 screw lamp holder. While an Edison-type connector 112 is illustrated in FIG. 6, any suitable connector may be used. In embodiments, the lighting element 110 may include a body 114 extending away from the connector 112 and including a plurality of openings 116 separated and defined by vertical ribs 115. In embodiments, the openings 116 are provided substantially around the entire periphery of the body 114, however, different patterns and positioning of the openings 116 and ribs 115 may be used, as desired. In embodiments, the openings 116 and ribs 115 are positioned to prevent users from passing their fingers through the ribs 115 and into the openings to prevent accidental injury.

Figure 7:
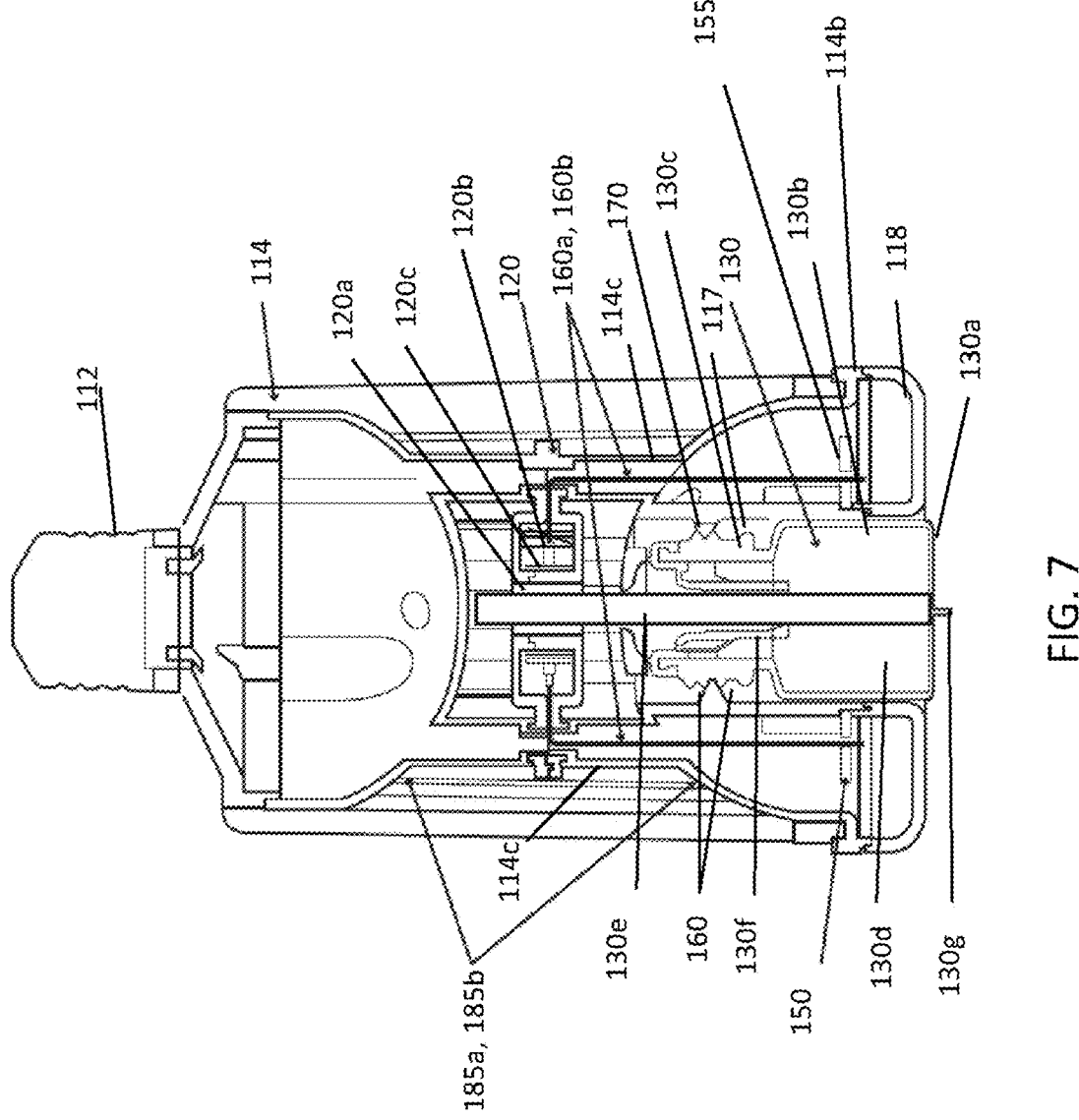
FIG. 7 illustrates a cross-sectional view of the lighting element of FIG. 6 in accordance with an embodiment of the present disclosure.

FIG. 7 illustrates a cross-sectional view of the lighting element 110. In embodiments, a heating element 120 may be provided inside the housing 114. In embodiments, the heating element 120 may be positioned substantially in a center of the housing 114. In embodiments, the heating element 120 may be positioned in any desired position in the housing 114. In embodiments, the heating element 120 may be disk shaped, however, other shapes may be used. In embodiments, the heating element 120 may include a central opening 120a and may be powered electrically via power provided from the connector 112. In embodiments, the heating element 120 may be directly connected to the connector 112. In embodiments, a heating circuit (not shown) may be provided between the connector 112 and the heating element 120 to provide power to the heating element. In embodiments, the heating circuit may be provided on a printed circuit board. In embodiments, the heating circuit may be implemented using discrete circuit elements. In embodiments, the heating circuit may be embodied as a processor or connected to and/or controlled by a processor or other control circuit. In embodiments, the heating circuit may be provided on printed circuit board 155 provided on a top surface of the bottom element 114b of the housing 114 (see FIG. 7, for example). In embodiments, the bottom element 114b may be attached to the rest of the housing 114 such that it prevents water from entering. In embodiments, the housing 114 may include one or more sleeves 114c that extend the length of the body 114 and in which wires 160a, 160b may run from the connector 112 to the PCB 155. In embodiments, additional or fewer sleeves 114c may be provided. The wires 160a. 160b may provide power to the PCB 155 and any circuit or circuit elements provided thereon.

In embodiments, an insect repelling material cartridge 130 may be mounted inside the housing 114. In embodiments, the insect repelling material cartridge 130 may include a bottom 130a with sidewalls 130b extending upward therefrom to a top portion 130c. In embodiments, an internal cavity 130d may contain insect repelling material. In embodiments, the insect repelling material may be in the form of a liquid, polymer and/or a gel, to name a few. In embodiments, the insect repelling material may be provided in an immersive foam solvent. In embodiments, the immersive foam solvent may hold the insect repelling material such that it will travel through the wick 130e even when the lighting element 110 is inverted. In embodiments, the immersive foam solvent may be removable to allow for easy refilling of the cartridge 130. In embodiments, the immersive foam solvent may not be replaceable and insect repelling material may be added thereto without removing it from the cartridge 130. In embodiments, the cartridge 130 may be entirely removed in order to replenish the insect repelling material. In embodiments, the cartridge 130 may be replaced by a new cartridge. In embodiments, the cartridge 130 may also include a wick element 130*e* that extends into the cavity 130*d* and into the insect repelling material and out of the open top 130*c* of the cartridge 130. In embodiments, an insert 130*f* may be provided in the open top of the cartridge 130 and includes an opening to allow the wick 130*e* to pass through while preventing leakage of the insect repelling material from the cartridge. In embodiments, the insect repelling material may be drawn up the wick 130*e* to the end thereof which is preferably positioned at least partially within the central opening 120*a* in the heating element 120 such that heat from the heating element 120 vaporizes the insect repelling material. In embodiments, the heating element 120 utilizes positive temperature coefficient (PTC) materials 120*b* for heating. In embodiments, the heating element 120 may use a resistive heating. In embodiments, a conductive ring 120*c* may be provided around the inner surface of the central opening 120*a* to conduct heat toward the wick 130*e*. In embodiments, the conductive ring 120*c* may be made of aluminum. In embodiments, the insect repelling material may be or include an insect repellant, which, after it is vaporized by the heating element 120, passes through the openings 116 and outward around the lighting element 10. In embodiments, the insect repelling material may include metofluthrin. As a result, a zone of vaporized insect repellant will surround the lighting element 10 which will deter insects from entering this zone. In embodiments, the insect repelling material may include insect repellant as well as an air freshening material such that the vaporized material will deter insects and will also provide a pleasant smell. In embodiments, the insect repelling material may be an air freshener only. In embodiments, the insect repelling material may include an air freshener material as well to provide a pleasant odor as well as insect repelling features.

In embodiments, the cartridge 130 may be removably mounted in the housing 114. In embodiments, the housing 114 may include fitting 117 which receives the cartridge 130. In embodiments, the cartridge 130 may include threads 160 which may interact with the fitting 117 to secure the cartridge in the housing 114. In embodiments, the fitting 117 may be annular in shape and include a central opening with threads 170 complimentary to the threads 160 of the cartridge 130. In embodiments, the fitting 117 and the cartridge 130 may be structured and positioned such that the wick 130*e* is positioned, at least partially, in the central opening 120*a* of the heating element 120 when the cartridge is mounted in the housing 114. In embodiments, the bottom of the cartridge 130 includes a tab 130*g* extending therefrom that may be gripped by a user to rotate the cartridge in a first direction to secure the cartridge to the housing 114 and/or in a second direction to remove the cartridge from the housing. In embodiments, the cartridge 130 may be substantially similar to the cartridge 30. In embodiments, the cartridge 130 may vary from the cartridge 30 in size, shape or otherwise.

In embodiments, the housing 114 may include a lower hemispherical protrusion 185*a*, positioned below the heating device 120, and an upper hemispherical protrusion 185*b* positioned above the heating device 120. In embodiments, the lower and upper hemispherical protrusions 185*a*, 185*b* are positioned such that air flows along the surface of one, toward the heating element 120 and the heated air and vaporized insect repelling material then passes along the surface of the other hemispherical protrusion and out of the housing 114 through the openings 116. Since the protrusions 185*a*, 185*b* are positioned both above and below the heating element 120, air flow, and the flow of vaporized insect repelling material, will be substantially the same whether the housing 114 is upright or inverted. The hemispherical shape of the protrusions 185*a*, 185*b* provides for the desired air and vapor flow described above. Thus, the lighting element 110 will operate efficiently regardless of orientation of the socket in which the connector 112 is received.

In embodiments, a light source 118 may be provided on a surface of the bottom portion 114*b* of the housing 114. In embodiments, the light source 118 may be implemented in the form of one or more light emitting diodes (LEDs) 118*b*. In embodiments, the light source 118 may be implemented as any other suitable light element or elements. In embodiments, the light source 118 may be electrically powered with power provided via the connector 112. In embodiments, the light source 18 may be directly connected to the connector 112. In embodiments, a light circuit (not shown) may be provided between the connector 112 and the light source 118 to provide power to the light source. In embodiments, the light circuit may be provided on a printed circuit board. In embodiments, the light circuit may be implemented as discrete circuit elements. In embodiments, the light circuit may be embodied as a processor or connected to and/or controlled by a processor or other control element or circuit. In embodiments, the light circuit may be provided on printed circuit board 155 provided on the lower portion 114*b* of the housing 114. In embodiments the light circuit and heat circuit discussed above may both be provided on the PCB 155. In embodiments, the light circuit and heat circuit may be separated on different portion of the PCB 155 or on different printed circuit boards. In embodiments, the PCB 155 may be divided into one or more segments. In embodiments, a lamp lens or other cover 118*a* may cover LEDs or other light elements. In embodiments, the cover 118*a* may be substantially transparent. In embodiments, the cover 118*a* may be substantially opaque. In embodiments the cover 118*a* may be partially opaque. In embodiments, the cover 118*a* may be colored to provide for a colored light.

Figure 7A:
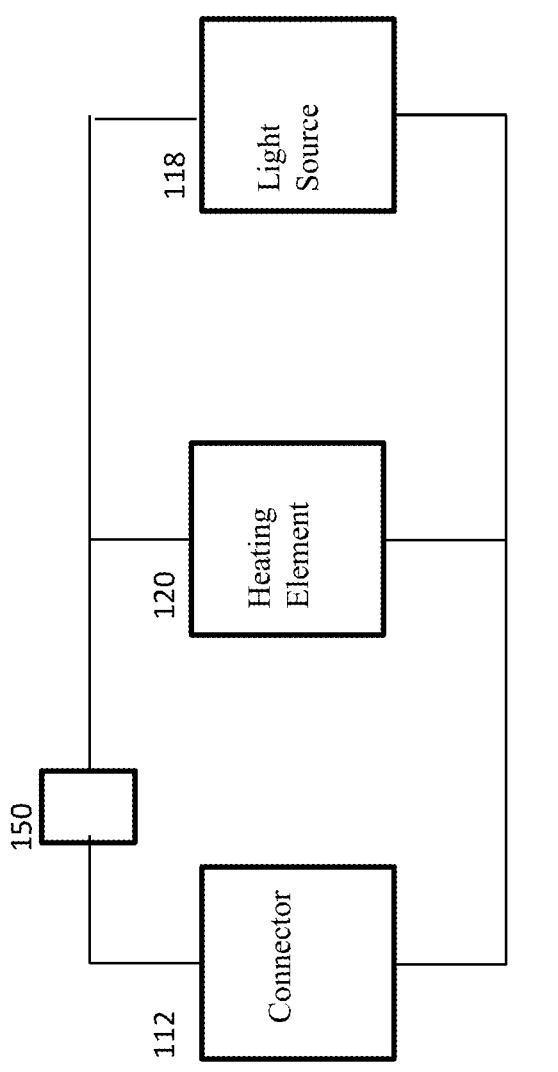
FIG. 7A is an exemplary block diagram illustrating a connection between an electrical connector, a switch, a heating element and a light source of the lighting element of FIG. 6.
Figure 8:
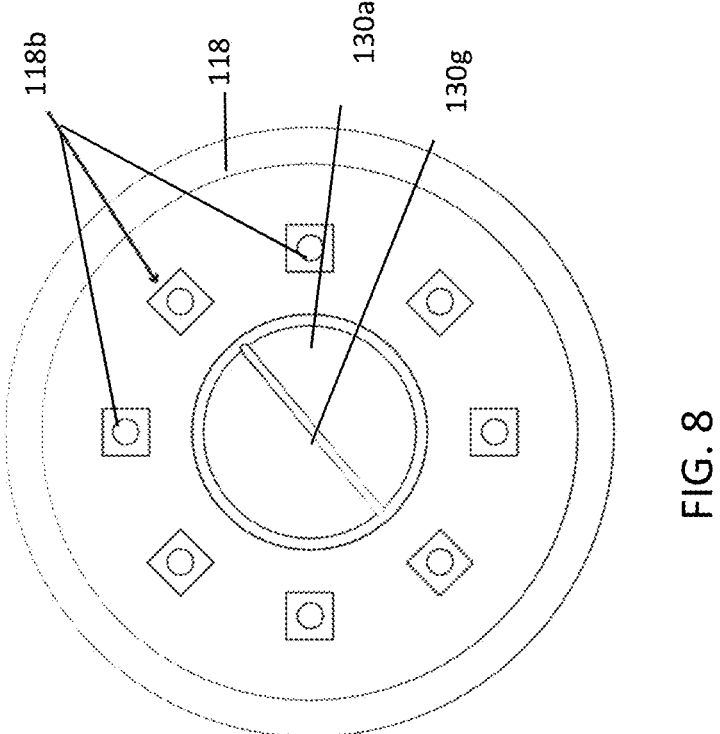
FIG. 8 illustrates a bottom view of the lighting element of FIG. 6 in accordance with an embodiment of the present disclosure.
Figure 9:
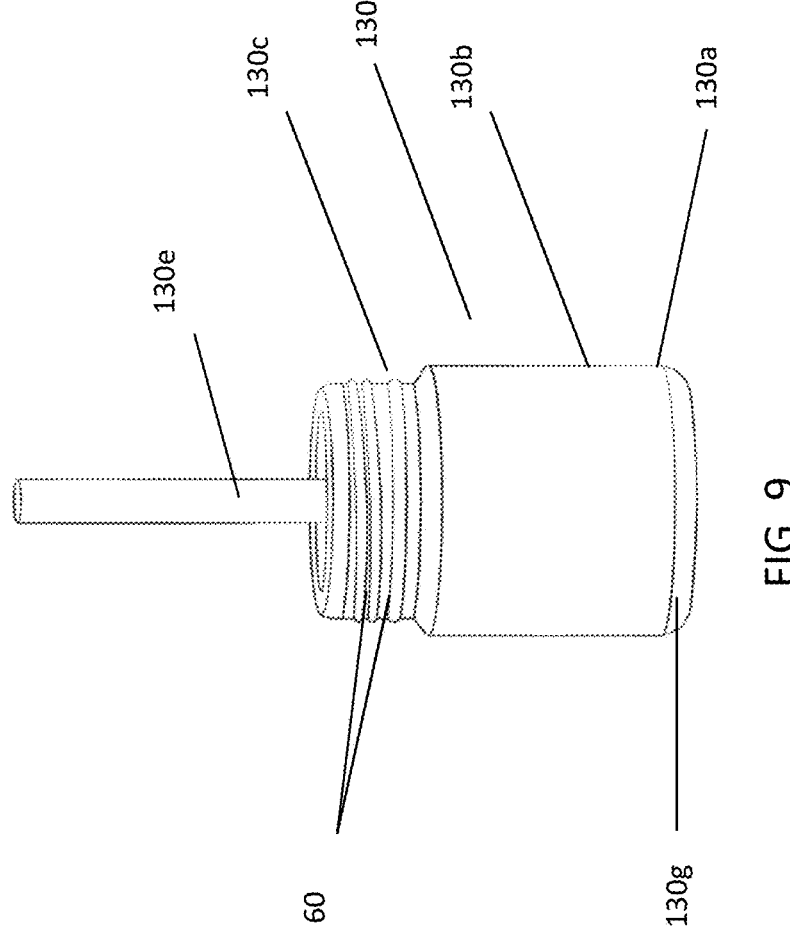
FIG. 9 is a more detailed view of the inset repelling material cartridge of the lighting element of FIG. 6.

In embodiments, both the heating element 120 and the light source 118 may be selectably activated by a user. In embodiments, one or more switch 150 may be provided to control power delivered to the heating element 120 and/or the light source 118. In embodiments, the one or more switch 150 may be used to activate the hearting circuit or lighting circuit discussed above. FIG. 7A illustrates an exemplary block diagram illustrating an exemplary connection between the connector 112 which provides power, via switch 150, to the heating element 120 and light source 118 (or a light element thereof). While a single switch 150 is illustrated in FIG. 7A, additional switches may be provided to allow for control of the heating element 120 and the light source 118 independently. In embodiments, the switch 150 may be a multiple position switch to allow for control of the heating element 120 and the light source 118 independently or together. In embodiments, the switch 150 may be embodied as a programmable device or controller to allow for control of the heating element 120 and the light source 118 independently or together. In embodiments, one or more timers may be used to control activation of the heating element 120 and/or light source 118. In embodiments, one or more timers may be used in combination with the one or more switches. In embodiments, the one or more switches may be used to activate the one or more timers. In embodiments, the one or more timers may be used to activate one or more switches. In embodiments, one or more light sensors may be provided and activation of the heating element 120 and/or light source 118 may be based on a detected light level. In embodiments, the heating element 120 may be activated without activating the light source 118 to provide for insect repelling even when light is unnecessary, for example, during the day. In embodiments, the light element 118 may be activated while the heating element 120 remains inactive such that light is provided even if there is no need for insect repellant. Both the light source 118 and heating element 120 may be activated at the same time to provide light as well as insect repellant. The light source 118 and heating element 120 may be deactivated at the same time as well. In embodiments, one or more indicators 195 may be provided to indicate that the heater 120 is active. In embodiments, the indicator 195 may be a light emitting diode or other light element. In embodiments, the indicator may be an audible indicator.

The lighting element 10, 110 of the present application thus provides for light, when desired, while also deterring insects from gathering near the light. Further, the light and insect repelling portions may be selectively activated to provide one without the other or both at the same time. Thus, the lighting element 10, 110 of the present application will allow users to enjoy the outdoors in the evening without the bother of active insects.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A lighting element with volatile substance comprises:
an electrical connector configured for connection to an external power source;
a body extending from the electrical connector, the body including a plurality of openings formed in a side thereof;
a heating element mounted in the body and electrically connected to the electrical connector;
a volatile substance cartridge including a volatile substance, the volatile substance cartridge removably mounted in the body, the volatile substance cartridge including:
a bottom;
sidewalls extending upward from the bottom to form a cavity, where the cavity receives volatile substance;
an open top;
a wick extending from the cavity to the open top to transfer volatile substance from the cavity of the volatile substance cartridge,
the volatile substance cartridge mounted in the body such that a top portion of the wick is adjacent to the heating element such that heat from the heating element vaporizes the volatile substance in the wick;
a light source, mounted on a bottom surface of a bottom of the body and electrically connected to the electrical connector, the light source configured to emit light; and
a plurality of vertical ribs extending away from the electrical connector and spaced laterally from each other such that a plurality of openings are provided between the plurality of vertical ribs.

2. The lighting element of claim 1, wherein the volatile substance is an air freshener substance.

3. The lighting element of claim 1, wherein each opening of the plurality of openings is sized such that a user's finger will not fit into the respective opening.

4. The lighting element of claim 1, wherein the heating element is disk shaped.

5. The lighting element of claim 4, wherein the heating element further comprises a central opening formed therethrough, and the volatile substance cartridge is mounted in the body such that at least a portion of the wick extends into the central opening of the heating element.

6. The lighting element of claim 5, wherein the heating element further comprises:
positive temperature coefficient material configured to produce heat; and
a conducting ring positioned around an inner surface of the central opening to conduct heat toward the wick.

7. The lighting element of claim 1, wherein the volatile substance cartridge further comprises an insert configured to be mounted in the open top of the volatile substance cartridge, the insert including a wick opening formed therein to allow the wick to pass through the insert while preventing volatile substance from passing around the insert and out of the volatile substance cartridge.

8. The lighting element of claim 1, wherein the volatile substance is provided in an immersive foam solvent.

9. The lighting element of claim 1, wherein the volatile substance is one of a group comprising a liquid, a polymer and a gel.

10. The lighting element of claim 1, wherein the body further comprises a receptacle formed in a bottom element of the body.

11. The lighting element of claim 10, wherein the volatile substance cartridge is removably mounted in the receptacle.

12. The lighting element of claim 11, wherein the volatile substance cartridge further comprises a tab extending from a bottom surface of the bottom thereof and configured to allow a user to rotate the volatile substance cartridge in the receptacle to secure the volatile substance cartridge in the receptacle when rotated in a first direction and to remove the volatile substance cartridge from the receptacle when rotated in a second direction, opposite the first direction.

13. The lighting element of claim 1, wherein the body further comprises:
a lower protrusion extending upward from an inner surface of a bottom portion of the body and positioned below the heating element; and
an upper protrusion extending downward from an inner surface of a top portion of the body above the heating element,
wherein the upper protrusion and lower protrusion are configured such that air flows along a surface of one of the upper protrusion and the lower protrusion toward the heating element and then along the surface of the other of the upper protrusion and the lower protrusion and then out through the plurality of openings.

14. The lighting element of claim 1, further comprising at least one indicator configured to indicate that the heating element is active.

15. The lighting element of claim 14, wherein the at least one indicator is a light emitting diode.

16. The lighting element of claim 15, wherein the at least one indicator is a transducer that emits sound.

17. The lighting element of claim 1, wherein the light source is a light emitting diode.

18. The lighting element of claim 17, wherein the light source further comprises a cover element positioned to cover the light emitting diode.

19. The lighting element of claim 18, wherein the cover element is colored.

\* \* \* \* \*